United States Patent
Coleman et al.

(10) Patent No.: US 8,138,318 B2
(45) Date of Patent: Mar. 20, 2012

(54) HEPATITIS B PRE-S2 NUCLEIC ACID

(75) Inventors: Paul F. Coleman, Antioch, IL (US);
Sandra K. Pearce, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/209,093

(22) Filed: Sep. 11, 2008

(65) Prior Publication Data
US 2009/0104712 A1    Apr. 23, 2009

Related U.S. Application Data

(60) Provisional application No. 60/972,142, filed on Sep. 13, 2007.

(51) Int. Cl.
*A61K 39/29* (2006.01)
*C12N 15/51* (2006.01)

(52) U.S. Cl. .................. 536/23.1; 424/227.1; 435/69.1

(58) Field of Classification Search .................. None
See application file for complete search history.

(56) References Cited

U.S. PATENT DOCUMENTS

| | | | |
|---|---|---|---|
| 5,006,309 A | 4/1991 | Khalil et al. | |
| 5,034,506 A | 7/1991 | Summerton et al. | |
| 5,063,081 A | 11/1991 | Cozzette et al. | |
| 5,089,424 A | 2/1992 | Khalil et al. | |
| 5,235,033 A | 8/1993 | Summerton et al. | |
| 5,925,512 A | 7/1999 | Carman et al. | |
| 6,884,629 B2 * | 4/2005 | Gore et al. | 436/547 |
| 7,141,242 B2 | 11/2006 | Coleman et al. | |
| 2002/0115080 A1 | 8/2002 | Skouv et al. | |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2005/0107325 A1 | 5/2005 | Manoharan et al. | |
| 2005/0182005 A1 | 8/2005 | Tuschl et al. | |
| 2006/0160164 A1 | 7/2006 | Miller et al. | |

FOREIGN PATENT DOCUMENTS

| | | |
|---|---|---|
| EP | 0196056 | 5/1991 |
| EP | 0331961 | 12/1995 |
| WO | WO9412617 A1 * | 6/1994 |
| WO | 2005/056051 | 6/2005 |
| WO | 2009/036228 | 3/2009 |

OTHER PUBLICATIONS

Qin, et al. World Journal of Gastroenterology (2003), 9(5),pp. 1111-1114.*
Tien et al. Zoological Studies , 1994, vol. 33, No. 2, pp. 140-152.*
Krutzfeldt, et. al., Nature, "Silencing of MicroRNAs in vivo with 'antagomirs'", vol. 438, 685-689 (2005).
Soutschek, et. al., Nature, "Therapeutic Silencing of an Endogenous Gene by Systemic Administration of Modified SiRNAs", vol. 432, 173-178 (2004).
Sambrook, et. al., Table of Contents, Molecular Cloning: A Laboratory Manual,(2001).
Coleman, et. al., "Immunoassay Detection of Hepatitis B Surface Antigen Mutants", J of Med Viro, 59:19-24 (1999).
De Maddalena et. al., "High Level of Genetic Heterogeneity in S and P Genes of Genotype D Hepatitis B Virus", Virology, Academic Press, Orlando, US, vol. 365. No. 1, 113-124, (2007).
& Database NCBI, Database accession No. EF514267 abstract, (Jul. 19, 2007) XP002511122.

* cited by examiner

*Primary Examiner* — Bao Li
(74) *Attorney, Agent, or Firm* — Cheryl L. Becker

(57) ABSTRACT

This invention relates to a nucleic acid molecule encoding a middle Hepatitis B virus (HBV) surface protein, a vector comprising the nucleic acid molecule, a host cell comprising the vector, and a composition comprising the expression products of this vector, which may comprise middle HBV surface protein, or a mixture of middle HBV surface protein and small HBV surface protein. The compositions of the invention may be useful for expressing a middle HBV surface protein, or a mixture of small and middle HBV surface proteins in defined ratios, determining the binding of an antibody to a middle or small HBV surface protein, determining the quality of an anti-middle or an anti-small HBV surface protein antibody, or determining the quality of a kit containing anti-middle or anti-small HBV surface protein antibodies.

13 Claims, 6 Drawing Sheets

| Sample | Dilution | Auszyme Monoclonal S/CO | Architect HBsAg S/CO |
|---|---|---|---|
| MHB | 1:10 | 57.27 | 213.50 |
| MHB-Kozak AAG | 1:10 | 20.16 | 44.15 |
| MHB-Kozak GAG | 1:10 | 30.40 | 74.08 |
| MHB-Kozak GAG-M1L | 1:10 | 2.89 | 5.77 |
| SHB | 1:10 | 14.20 | 46.28 |
| pc DNA | 1:10 | 0.08 | 0.66 |
| UTF | 1:10 | 0.11 | 0.49 |
| plasma | neat | 0.10 | NT |
| AdA | neat | 5.26 | NT |
| neg ctl | neat | 0.15 | 0.48 |
| pos ctl | neat | 18.12 | 4.32 |

NT = not tested

FIG.6

SEQUENCE LISTING

```
<160> NUMBER OF SEQ ID NOS: 26

<210> SEQ ID NO 1
<211> LENGTH: 281
<212> TYPE: PRT
<213> ORGANISM: Hepatitis B virus

<400> SEQUENCE: 1

Met Gln Trp Asn Ser Thr Ala Phe His Gln Ala Leu Gln Asp Pro Arg
1               5                   10                  15

Val Arg Gly Leu Tyr Phe Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Val Thr Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Ser Pro Val Cys Leu Gly Gln Asn Ser Gln Ser Pro Thr
            100                 105                 110

Ser Asn His Ser Pro Thr Ser Cys Pro Pro Ile Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Thr Thr Thr Ser Thr Gly Pro Cys
                165                 170                 175

Lys Thr Cys Thr Thr Pro Ala Gln Gly Asn Ser Met Phe Pro Ser Cys
            180                 185                 190

Cys Cys Thr Lys Pro Thr Asp Gly Asn Cys Thr Cys Ile Pro Ile Pro
        195                 200                 205

Ser Ser Trp Ala Phe Ala Lys Tyr Leu Trp Glu Trp Ala Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Ala Ile Trp Met Met Trp Tyr Trp
                245                 250                 255

Gly Pro Ser Leu Tyr Ser Ile Val Ser Pro Phe Ile Pro Leu Leu Pro
            260                 265                 270

Ile Phe Phe Cys Leu Trp Val Tyr Ile
```

```
                275                 280
```

<210> SEQ ID NO 2
<211> LENGTH: 846
<212> TYPE: DNA
<213> ORGANISM: Hepatitis B virus

<400> SEQUENCE: 2

| | | | | | |
|---|---|---|---|---|---|
| atgcagtgga | attccactgc | cttccaccaa | gctctgcaag | atcccagagt | cagggggtctg | 60 |
| tattttcctg | ctggtggctc | cagttcagga | acagtaaacc | ctgctccgaa | tattgcctct | 120 |
| cacatctcgt | caatctccgc | gaggactggg | gaccctgtga | cgaacatgga | gaacatcaca | 180 |
| tcaggattcc | taggacccct | gctcgtgtta | caggcggggt | ttttcttgtt | gacaagaatc | 240 |
| ctcacaatac | cgcagagtct | agactcgtgg | tggacttctc | tcaattttct | aggggggatca | 300 |
| cccgtgtgtc | ttggccaaaa | ttcgcagtcc | ccaacctcca | atcactcacc | aacctcctgt | 360 |
| cctccaattt | gtcctggtta | tcgctggatg | tgtctgcggc | gttttatcat | attcctcttc | 420 |
| atcctgctgc | tatgcctcat | cttcttattg | gttcttctgg | attatcaagg | tatgttgccc | 480 |
| gtttgtcctc | taattccagg | atcaacaaca | accagtacgg | gaccatgcaa | aacctgcacg | 540 |
| actcctgctc | aaggcaactc | tatgtttccc | tcatgttgct | gtacaaaacc | tacggatgga | 600 |
| aattgcacct | gtattcccat | cccatcgtcc | tgggctttcg | caaaatacct | atgggagtgg | 660 |
| gcctcagtcc | gtttctcttg | gctcagttta | ctagtgccat | ttgttcagtg | gttcgtaggg | 720 |
| ctttccccca | ctgtttggct | ttcagctata | tggatgatgt | ggtattgggg | gccaagtctg | 780 |
| tacagcatcg | tgagtccctt | tataccgctg | ttaccaattt | tcttttgtct | ctgggtatac | 840 |
| atttaa | | | | | | 846 |

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 cttatgcag                                                          9

<210> SEQ ID NO 4
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, t, g or c

<400> SEQUENCE: 4 rnnatgg                                                            7

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gagatgcag                                                                    9

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 aagatgcag                                                                    9

<210> SEQ ID NO 7
<211> LENGTH: 848
<212> TYPE: DNA
<213> ORGANISM: Hepatitis B virus

<400> SEQUENCE: 7
gagatgcagt ggaattccac tgccttccac caagctctgc aagatcccag agtcaggggt           60
ctgtattttc ctgctggtgg ctccagttca ggacagtaaa ccctgctccg aatattgcct          120
ctcacatctc gtcaatctcc gcgaggactg gggaccctgt gacgaacatg gagaacatca          180
catcaggatt cctaggaccc ctgctcgtgt tacaggcggg gttttcttg ttgacaagaa           240 tcctcacaat accgcagagt ctagactcgt ggtggacttc tctcaatttt ctaggggat           300 cacccgtgtg tcttggccaa aattcgcagt ccccaacctc caatcactca ccaacctcct          360
gtcctccaat ttgtcctggt tatcgctgga tgtgtctgcg gcgttttatc atattcctct          420
tcatcctgct gctatgcctc atcttcttat tggttcttct ggattatcaa ggtatgttgc          480
ccgtttgtcc tctaattcca ggatcaacaa caaccagtac gggaccatgc aaaacctgca          540
cgactcctgc tcaaggcaac tctatgtttc cctcatgttg ctgtacaaaa cctacggatg          600
gaaattgcac ctgtattccc atcccatcgt cctgggcttt cgcaaaatac ctatgggagt          660
gggcctcagt ccgtttctct tggctcagtt tactagtgcc atttgttcag tggttcgtag          720
ggctttcccc cactgtttgg ctttcagcta tatggatgat gtggtattgg gggccaagtc          780
tgtacagcat cgtgagtccc tttataccgc tgttaccaat tttcttttgt ctctgggtat          840
acatttaa                                                                   848

<210> SEQ ID NO 8
<211> LENGTH: 849
<212> TYPE: DNA
<213> ORGANISM: Hepatitis B virus

<400> SEQUENCE: 8
aagatgcagt ggaattccac tgccttccac caagctctgc aagatcccag agtcaggggt           60
ctgtattttc ctgctggtgg ctccagttca ggaacagtaa accctgctcc gaatattgcc          120
tctcacatct cgtcaatctc cgcgaggact ggggaccctg tgacgaacat ggagaacatc          180
acatcaggat tcctaggacc cctgctcgtg ttacaggcgg ggttttcttt gttgacaaga          240
atcctcacaa taccgcagag tctagactcg tggtggactt ctctcaattt tctaggggga          300
tcacccgtgt gtcttggcca aaattcgcag tccccaacct ccaatcactc accaacctcc          360
tgtcctccaa tttgtcctgg ttatcgctgg atgtgtctgc ggcgttttat catattcctc          420
ttcatcctgc tgctatgcct catcttctta ttggttcttc tggattatca aggtatgttg          480
cccgtttgtc tctaattcc aggatcaaca acaaccagta cgggaccatg caaaacctgc           540
```

-continued

```
acgactcctg ctcaaggcaa ctctatgttt ccctcatgtt gctgtacaaa acctacggat    600
ggaaattgca cctgtattcc catcccatcg tcctgggctt tcgcaaaata cctatgggag    660
tgggcctcag tccgtttctc ttggctcagt ttactagtgc catttgttca gtggttcgta    720
gggctttccc ccactgtttg gctttcagct atatggatga tgtggtattg ggggccaagt    780
ctgtacagca tcgtgagtcc ctttataccg ctgttaccaa ttttcttttg tctctgggta    840
tacatttaa                                                            849
```

<210> SEQ ID NO 9
<211> LENGTH: 226
<212> TYPE: PRT
<213> ORGANISM: Hepatitis B virus

<400> SEQUENCE: 9

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225
```

<210> SEQ ID NO 10
<211> LENGTH: 681
<212> TYPE: DNA
<213> ORGANISM: Hepatitis B virus

<400> SEQUENCE: 10

```
atggagaaca tcacatcagg attcctagga ccccctgctcg tgttacaggc ggggttttc    60 ttgttgacaa gaatcctcac aataccgcag agtctagact cgtggtggac ttctctcaat   120
tttctagggg gatcacccgt gtgtcttggc caaaattcgc agtccccaac ctccaatcac   180
tcaccaacct cctgtcctcc aatttgtcct ggttatcgct ggatgtgtct gcggcgtttt   240
```

-continued

```
atcatattcc tcttcatcct gctgctatgc ctcatcttct tattggttct tctggattat    300
caaggtatgt tgcccgtttg tcctctaatt ccaggatcaa caacaaccag tacgggacca    360
tgcaaaacct gcacgactcc tgctcaaggc aactctatgt ttccctcatg ttgctgtaca    420
aaacctacgg atggaaattg cacctgtatt cccatcccat cgtcctgggc tttcgcaaaa    480
tacctatggg agtgggcctc agtccgtttc tcttggctca gtttactagt gccatttgtt    540
cagtggttcg tagggctttc ccccactgtt tggctttcag ctatatggat gatgtggtat    600
tgggggccaa gtctgtacag catcgtgagt cccttatac cgctgttacc aatttttcttt    660 tgtctctggg tatacattta a                                              681
```

<210> SEQ ID NO 11
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 aacatgg                                                              7

<210> SEQ ID NO 12
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 aacttgg                                                              7

<210> SEQ ID NO 13
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 aacctgg                                                              7

<210> SEQ ID NO 14
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
aacttggaga acatcacatc aggattccta ggacccctgc tcgtgttaca ggcggggttt    60
ttcttgttga caagaatcct cacaataccg cagagtctag actcgtggtg gacttctctc    120
aattttctag ggggatcacc cgtgtgtctt ggccaaaatt cgcagtcccc aacctccaat    180
cactcaccaa cctcctgtcc tccaatttgt cctggttatc gctggatgtg tctgcggcgt    240
tttatcatat tcctcttcat cctgctgcta tgcctcatct tcttattggt tcttctggat    300
tatcaaggta tgttgcccgt ttgtcctcta attccaggat caacaacaac cagtacggga    360
ccatgcaaaa cctgcacgac tcctgctcaa ggcaactcta tgtttccctc atgttgctgt    420
```

```
acaaaaccta cggatggaaa ttgcacctgt attcccatcc catcgtcctg ggctttcgca      480 aaataccta  gggagtgggc ctcagtccgt ttctcttggc tcagtttact agtgccattt      540
gttcagtggt tcgtagggct ttcccccact gtttggcttt cagctatatg gatgatgtgg      600
tattgggggc caagtctgta cagcatcgtg agtccctttta taccgctgtt accaattttc      660
ttttgtctct gggtatacat ttaa                                             684

<210> SEQ ID NO 15
<211> LENGTH: 1203
<212> TYPE: DNA
<213> ORGANISM: Hepatitis B virus

<400> SEQUENCE: 15
atgggaggtt ggtcttccaa acctcgaaaa ggcatgggga caaatctttc tgtccccaat       60
cccctgggat tcttccccga tcatcagttg daccctgcat tcaaagccaa ctcagaaaat      120
ccagattggg acctcaaccc acacaaggac aactggccgg acgctcacaa ggtgggagtg      180
ggagcattcg ggccagggtt caccccctccc catgggggac tgttggggtg agccctcag      240 gctcagggca tactcacatc tgtgccagca gctcctcctc ctgcctccac caatcggcag      300
tcaggaaggc agcctactcc cttatctcca cctctaaggg cactcatcc tcaggccatg       360 cagtggaatt ccactgcctt ccaccaagct ctgcaagatc ccagagtcag gggtctgtat      420
tttcctgctg gtggctccag ttcaggaaca gtaaaccctg ctccgaatat tgcctctcac      480
atctcgtcaa tctccgcgag gactgggac cctgtgacga acatggagaa catcacatca      540
ggattcctag gacccctgct cgtgttacag gcggggtttt tcttgttgac aagaatcctc      600
acaataccgc agagtctaga ctcgtggtgg acttctctca attttctagg gggatcaccc      660
gtgtgtcttg gccaaaattc gcagtcccca acctccaatc actcaccaac ctcctgtcct      720
ccaatttgtc ctggttatcg ctggatgtgt ctgcggcgtt ttatcatatt cctcttcatc      780
ctgctgctat gcctcatctt cttattggtt cttctggatt atcaaggtat gttgcccgtt      840
tgtcctctaa ttccaggatc aacaacaacc agtacgggac catgcaaaac ctgcacgact      900
cctgctcaag gcaactctat gtttccctca tgttgctgta caaaacctac ggatggaaat      960
tgcacctgta ttcccatccc atcgtcctgg gctttcgcaa ataccctatg ggagtgggcc     1020
tcagtccgtt tctcttggct cagtttacta gtgccatttg ttcagtggtt cgtagggctt     1080 tccccccactg tttggcttt agctatatgg atgatgtggt attgggggcc aagtctgtac     1140
agcatcgtga gtccctttat accgctgtta ccaattttct tttgtctctg ggtatacatt     1200
taa                                                                   1203

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gccrccatgg                                                             10

<210> SEQ ID NO 17
<211> LENGTH: 7
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 17 rccatgg                                                                    7

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, t, g or c

<400> SEQUENCE: 18 gnnatgcag                                                                  9

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, t, g or c

<400> SEQUENCE: 19 annatgcag                                                                  9

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggaattccac tgcatctcct taagtttaaa cgc                                       33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcgtttaaac ttaaggagat gcagtggaat tcc                                       33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggaattccac tgcatcttct taagtttaaa cgc                                       33

```
<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgtttaaac ttaagaagat gcagtggaat tcc                               33

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtgatgttct ccaagttcgt cacagg                                       26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cctgtgacga acttggagaa catcac                                       26

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Ser Thr Gly Pro Cys Thr Thr
1               5
```

HEPATITIS B PRE-S2 NUCLEIC ACID

The subject application claims priority to U.S. provisional application Ser. No. 60/972,142 filed on Sep. 13, 2007, herein incorporated in its entirety by reference.

FIELD OF THE INVENTION

This invention relates to hepatitis B virus nucleic acids, compositions comprising hepatitis B virus surface proteins, and methods and kits related thereto.

BACKGROUND OF THE INVENTION

Hepatitis B virus (HBV) has infected over 2 billion people worldwide. It causes a variety of disease conditions in humans ranging from mild subclinical infection to chronic active and fulminant hepatitis. Over 400 million people, especially children and the elderly, are chronically infected with HBV. Hepatitis B virus is 100 times more infectious than the AIDS virus, yet it can be prevented with vaccination. Thus, the focal point in combating HBV includes vaccination. A vaccine is of no use for those already infected with hepatitis B. If the virus is detected soon enough, however, treatment options are available for those chronically infected. Accordingly, diagnostic assays have focused on identifying target antigens of the HBV virus for sufficiently early detection.

The HBV genome is a circular, partially double-stranded DNA approximately 3200 base pairs in length, and encodes seven viral proteins. The HBV envelope consists of three glycosylated proteins (large, medium and small HBV surface proteins, or LHB, MHB, and SHB, respectively), which are encoded by the same gene, but are produced from three different initiation sites and share the same termination site. The three different regions of the envelope protein gene, preS1, preS2, and S, encode LHB, MHB, and SHB, respectively (See FIG. 1 and FIG. 2). These three proteins are expressed at different ratios and assemble to form the outer capsid of the HBV virion and also form an incomplete viral particle. HBV surface antigen assays detect both forms of expression products virions and particles.

Regions of the HBV proteins are exposed on HBV particle surfaces and may be the targets of immune surveillance. However, HBV exhibits a high mutation rate due to its essential reliance on reverse transcriptase (RT) in replication, and the poor proofreading ability of RT. Accordingly, HBV is capable of evading immune surveillance and vaccination regimens via mutations in the envelope proteins, including SHB. Furthermore, because some methods of HBV detection depend on monitoring epitopes within the envelope proteins by using anti-SHB antibodies, highly mutable HBV may also escape detection. There is hence a continued need in the art for methods and compositions for detecting HBV.

SUMMARY OF THE INVENTION

Provided herein is a nucleic acid molecule encoding a MHB, or a nucleic acid molecule substantially identical thereto, wherein the nucleic acid sequence thereof comprises a preS2 initiation sequence comprising SEQ ID NO: 4, 5, or 6. The sequence of the nucleic acid molecule may comprise SEQ ID NOs: 7 or 8. The nucleic acid molecule may further comprise a nucleotide sequence encoding a SHB, or a nucleotide sequence substantially identical thereto.

Also provided herein is a vector comprising the nucleic acid molecule and a host cell comprising the vector.

Further provided herein is a composition comprising a recombinant MHB at a concentration of $1 \times 10^{-12}$ to $1 \times 10^{-2}$ gms. The composition may further comprise recombinant SHB, which may be at a concentration of $1 \times 10^{-12}$ to $1 \times 10^{-2}$ gms. The MHB to SHB ratio in the composition may be between 1:1000 and 1000:1.

Also provided herein is a kit, which comprise the vector, the host cell, or the composition.

Further provided herein is a method of determining the binding of an antibody to MHB or a mixture of SHB and MHB. The method may comprise contacting a candidate antibody with the composition, and measuring the binding of the antibody to MHB or a mixture of SHB and MHB.

Also provided herein is a method of determining the quality of an antibody to MHB or a mixture of SHB and MHB, which may comprise providing a candidate antibody and determining the binding of the antibody to MHB or a mixture of SHB and MHB. The quality of the antibody may be determined by comparing the level of binding to a predetermined value.

Further provided herein is a method of determining the quality of a kit comprising an antibody to MHB or a mixture of SHB and MHB, which may comprise providing a candidate kit and determining the binding the antibody to MHB or a mixture of SHB and MHB. The quality of the kit may be determined by comparing the level of binding to a predetermined value.

BRIEF DESCRIPTION OF THE DRAWINGS

FIG. 2 also shows a schematic of the HBV surface proteins (LHB, MHB, and SHB) encoded by the preS1 nucleic acid.

FIG. 6 shows the average sample to cutoff (S/CO) results using the Auszyme Monoclonal or ARCHITECT HBsAg on-market Abbott diagnostic immunoassays.

DETAILED DESCRIPTION

Figure 1:
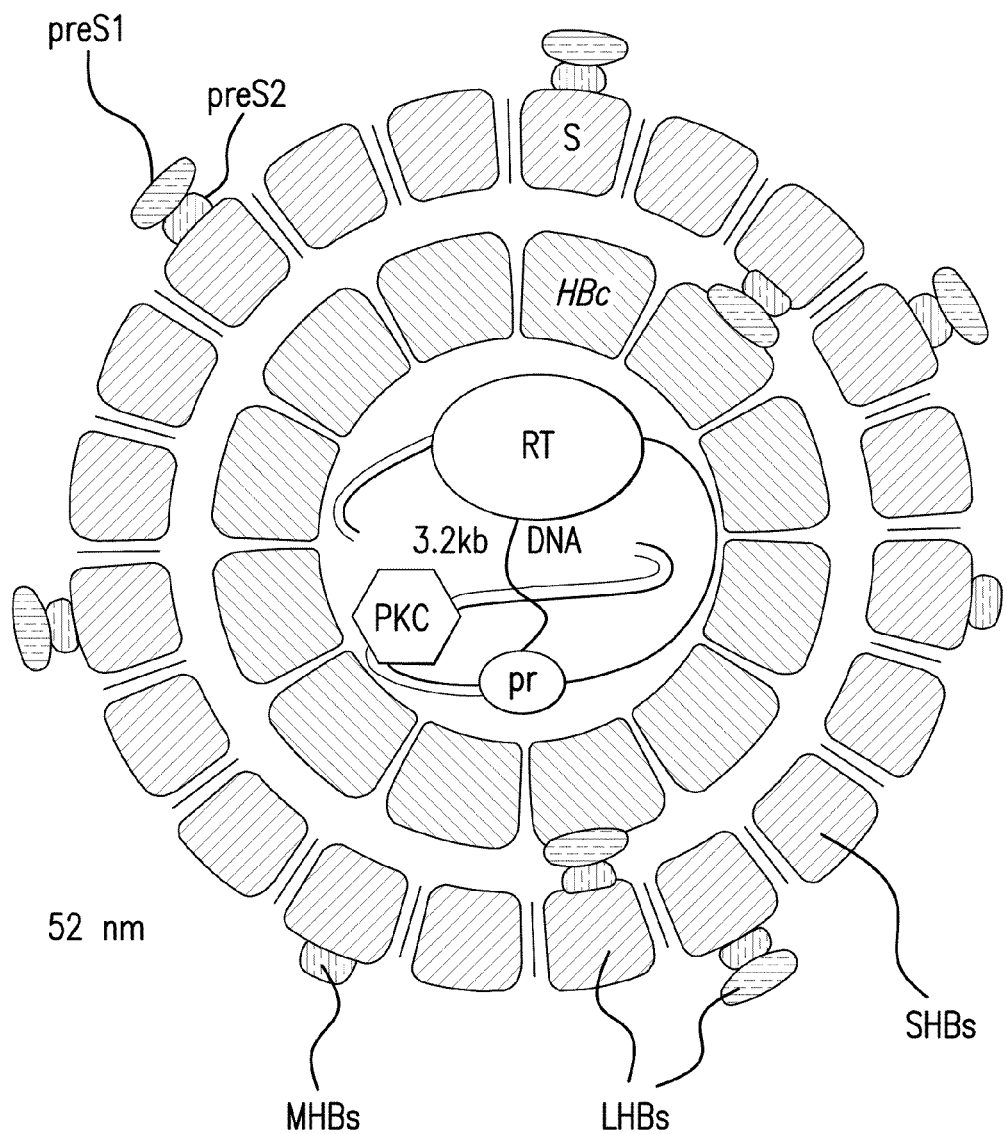
FIG. 1 is a schematic depiction of a HBV virion, including the mixture of HBV envelope protein constituents LHB, MHB, and SHB that have assembled to form the outer capsid. A similar assembly of these proteins form the incomplete particle (not shown).
Figure 2:
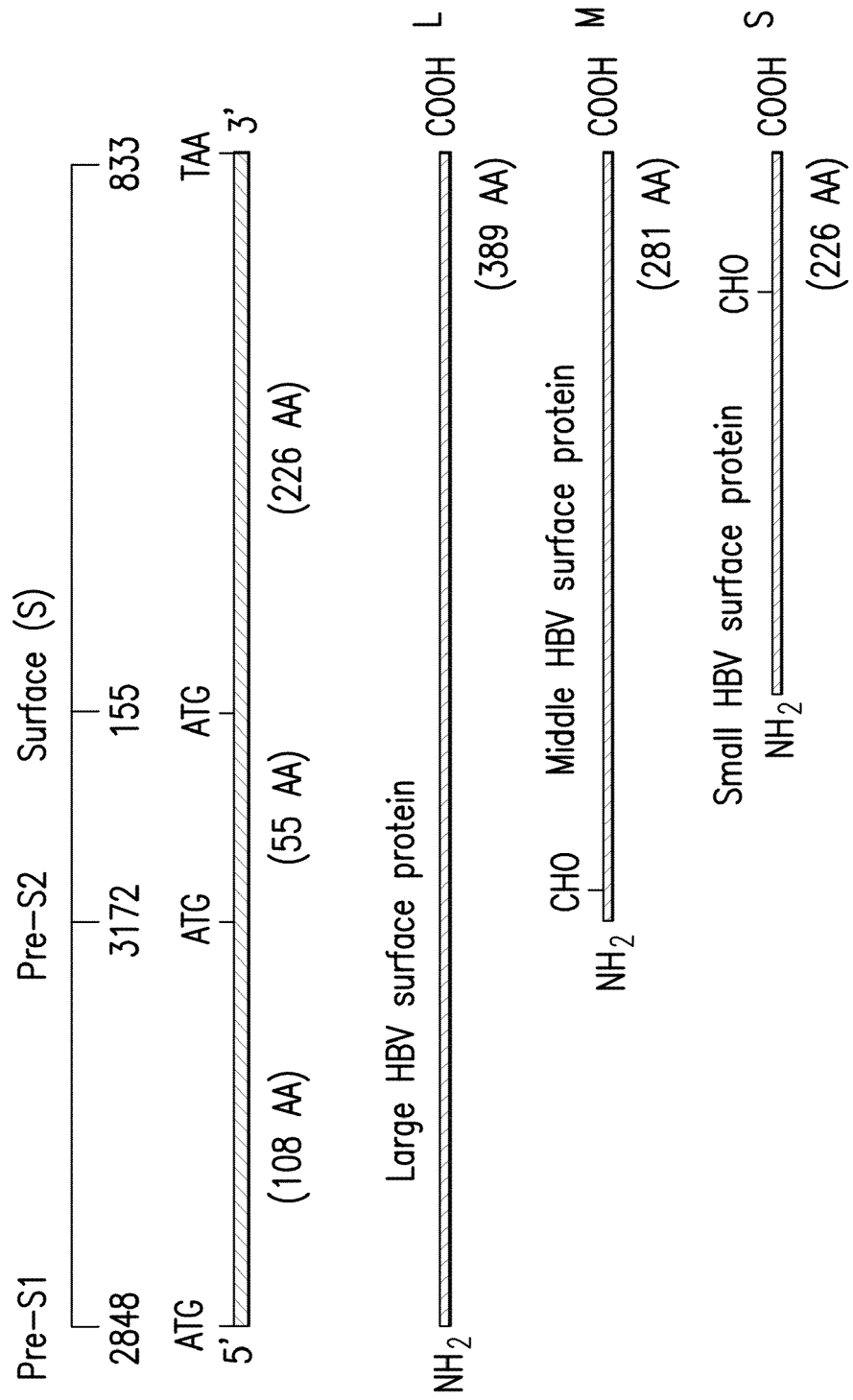
FIG. 2 shows a schematic depiction of the HBV preS1 open reading frame, and its preS2 and S regions.

Appropriate detection and quantification of HBV in clinical samples using an antibody-based approach may depend on a positive protein control or calibrator comprising an optimal mixture of both recombinant SHB and recombinant MHB. An expression system utilizing a non-Kozak preS2 initiation site and a wild-type Kozak S initiation site to express HBV surface proteins MHB and SHB, results in sub-optimal levels of MHB. The inventors have made the discovery that altering the preS2 initiation site from a non-Kozak sequence to a partial Kozak sequence results in a nucleic acid capable of expressing a mixture of HBV surface proteins MHB and SHB with an improved antigenicity ratio between these two proteins. Surprisingly, HBV surface protein expression using a partial Kozak preS2 initiation site introduced by mutation appears to more accurately reflect the ratio of SHB to MHB antigens seen in clinical samples. MHB expressed using such a modified sequence may be used alone, or with SHB at a known concentration or ratio as a positive control for testing reactivity of anti-HBV protein antibodies.

1. DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Antibody

"Antibody" as used herein may mean an antibody of classes IgG, IgM, IgA, IgD or IgE, or fragments or derivatives thereof, including Fab, F(ab')2, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

b. Attached

"Attached" or "immobilized" as used herein to refer to a polypeptide and a solid support may mean that the binding between the polypeptide and the solid support is sufficient to be stable under conditions of binding, washing, analysis, and removal. The binding may be covalent or non-covalent. Covalent bonds may be formed directly between the polypeptide and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated polypeptide to the streptavidin. Immobilization may also involve a combination of covalent and non-covalent interactions.

c. Coding Sequence

"Coding sequence" as used herein may mean a polynucleotide sequence which is transcribed into mRNA or translated into a polypeptide when placed under the control of appropriate regulatory sequences. The boundaries of the coding sequence may be determined by a translation start codon at the 5'-terminus and a translation stop codon at the 3'-terminus. A coding sequence may include a mRNA or recombinant polypeptide sequences.

d. Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules.

e. Epitope

"Epitope" or "antigen" as used herein may mean an antigenic determinant of a polypeptide. An epitope may comprise 3 amino acids in a spatial conformation which is unique to the epitope. An epitope may also comprise at least 4-10 amino acids. Methods of examining spatial conformation are known in the art and include, X-ray crystallography and two-dimensional nuclear magnetic resonance.

f. Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of the gene may be a nucleotide sequence coding for an amino acid sequence. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

g. Host Cell

"Host cell" as used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as COS-7, CHO and HeLa.

h. Identical

"Identical" or "identity" as used herein in the context of two or more polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

i. Label

"Label" or "detectable label" as used herein may mean a moiety capable of generating a signal that allows the direct or indirect quantitative or relative measurement of a molecule to which it is attached. The label may be a solid such as a microtiter plate, particle, microparticle, or microscope slide; an enzyme; an enzyme substrate; an enzyme inhibitor; coenzyme; enzyme precursor; apoenzyme; fluorescent substance; pigment; chemiluminescent compound; luminescent substance; coloring substance; magnetic substance; or a metal particle such as gold colloid; a radioactive substance such as $^{125}I$, $^{131}I$, $^{32}P$, $^{3}H$, $^{35}S$, or $^{14}C$; a phosphorylated phenol derivative such as a nitrophenyl phosphate, luciferin derivative, or dioxetane derivative; or the like. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyase; an isomerase; or a ligase. The enzyme may also be conjugated to another enzyme.

The enzyme may be detected by enzymatic cycling. For example, when the detectable label is an alkaline phosphatase, measurements may be made by observing the fluorescence or luminescence generated from a suitable substrate, such as an umbelliferone derivative. The umbelliferone derivative may comprise 4-methyl-umbellipheryl phosphate.

The fluorescent or chemiluminescent label may be a fluorescein isothiocyanate; a rhodamine derivative such as rhodamine β isothiocyanate or tetramethyl rhodamine isothiocyanate; a dancyl chloride (5-(dimethylamino)-1-naphtalenesulfonyl chloride); a dancyl fluoride; a fluorescamine (4-phenylspiro[furan-2(3H); 1ÿ-(3ÿH)-isobenzofuran]-3;3ÿ-dione); a phycobiliprotein such as a phycocyanine or physoerythrin; an acridinium salt; a luminol compound such as lumiferin, luciferase, or aequorin; imidazoles; an oxalic acid ester; a chelate compound of rare earth elements such as europium (Eu), terbium (Tb) or samarium (Sm); or a coumarin derivative such as 7-amino-4-methylcoumarin.

The label may also be a hapten, such as adamantine, fluoroscein isothiocyanate, or carbazole. The hapten may allow the formation of an aggregate when contacted with a multivalent antibody or (strep)avidin containing moiety. The hapten may also allow easy attachment of a molecule to which it is attached to a solid substrate.

The label may be detected by quantifying the level of a molecule attached to a detectable label, such as by use of electrodes; spectrophotometric measurement of color, light, or absorbance; or visual inspection.

j. Nucleic Acid

"Nucleic acid molecule" or "oligonucleotide" or "polynucleotide" used herein may mean at least two nucleotides covalently linked together. The depiction of a single strand also defines the sequence of the complementary strand. Thus, a nucleic acid molecule also encompasses the complementary strand of a depicted single strand. Many variants of a nucleic acid molecule may be used for the same purpose as a given nucleic acid. Thus, a nucleic acid molecule also encompasses substantially identical nucleic acid molecules and complements thereof. A single strand provides a probe that may hybridize to a target sequence under stringent hybridization conditions. Thus, a nucleic acid molecule also encompasses a probe that hybridizes under stringent hybridization conditions.

Nucleic acids molecules may be single stranded or double stranded, or may contain portions of both double stranded and single stranded sequence. The nucleic acid molecule may be DNA, both genomic and cDNA, RNA, or a hybrid, where the nucleic acid molecule may contain combinations of deoxyribo- and ribo-nucleotides, and combinations of bases including uracil, adenine, thymine, cytosine, guanine, inosine, xanthine hypoxanthine, isocytosine and isoguanine. Nucleic acid molecules may be obtained by chemical synthesis methods or by recombinant methods.

A nucleic acid molecule will generally contain phosphodiester bonds, although nucleic acid molecule analogs may be included that may have at least one different linkage, e.g., phosphoramidate, phosphorothioate, phosphorodithioate, or O-methylphosphoroamidite linkages and peptide nucleic acid backbones and linkages. Other analog nucleic acid molecules include those with positive backbones, non-ionic backbones, and non-ribose backbones, including those described in U.S. Pat. Nos. 5,235,033 and 5,034,506, which are incorporated by reference. Nucleic acid molecules containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'OH-group may be replaced by a group selected from H, OR, R, halo, SH, SR, NH2, NHR, NR2 or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference. Modified nucleotides and nucleic acid molecules may also include locked nucleic acids (LNA), as described in U.S. Patent No. 20020115080, which is incorporated herein by reference. Additional modified nucleotides and nucleic acid molecules are described in U.S. Patent Publication Nos. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made. Alternatively, mixtures of different nucleic acid molecule analogs, and mixtures of naturally occurring nucleic acids and analogs may be made.

k. Open Reading Frame

"Open reading frame" or "ORF" as used herein may refer to a region of a polynucleotide sequence which encodes a polypeptide. The ORF may represent a portion of a coding sequence or a total coding sequence.

l. Operably Linked

"Operably linked" used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. The promoter may comprise a T7, TP1, lactase, or metallothionine promoter.

m. Peptide

A "peptide" or "polypeptide" as used herein may mean a linked sequence of amino acids and may be natural, synthetic, or a modification or combination of natural and synthetic.

n. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

o. Recombinant Polypeptide

A "recombinant polypeptide" or "recombinant protein" as used herein may mean at least a polypeptide of genomic, semisynthetic or synthetic origin which by virtue of its origin or manipulation is not associated with all or a portion of the polynucleotide with which it is associated in nature or in the form of a library, or is linked to a polynucleotide other than that to which it is linked in nature. The recombinant polypeptide may not necessarily be translated from a designated nucleic acid sequence of HBV. The recombinant polypeptide may also be generated in any manner, including chemical synthesis or expression of a recombinant expression system, or isolated from HBV.

p. Selectable Marker

"Selectable marker" as used herein may mean any gene which confers a phenotype on a host cell in which it is expressed to facilitate the identification and/or selection of cells which are transfected or transformed with a genetic construct. Representative examples of selectable markers include the ampicillin-resistance gene (Ampr), tetracycline-resistance gene (Tcr), bacterial kanamycin-resistance gene (Kanr), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

q. Solid Support

"Solid support" or "solid phase" as used herein may be the walls of wells of a reaction tray, test tubes, polystyrene beads, magnetic beads, nitrocellulose strips, membranes, microparticles such as latex particles, and others. The solid support is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid supports include ionic, hydrophobic, covalent interactions and the like. The solid support may also be any material which is insoluble, or may be made insoluble by a subsequent reaction. The solid support may be chosen for its intrinsic ability to attract and immobilize the capture reagent. Alternatively, the solid support may retain an additional receptor which has the ability to attract and immobilize the capture reagent. The additional receptor may include a charged substance that is oppositely charged with respect to the capture reagent itself or to a charged substance conjugated to the capture reagent. As yet another alternative, the receptor molecule may be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid support thus may be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid support also may comprise any suitable porous material with sufficient porosity to allow access by detection antibodies and a suitable surface affinity to bind antigens. Microporous structures are generally preferred, but materials with gel structure in the hydrated state may be used as well. Such useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. Pat. App. Ser. No. 227,272, which is incorporated herein by reference.

r. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Moderate stringency conditions may mean pre-washing in a solution of 5×SSC, 0.5% SDS, 1.0 mM EDTA (pH 8.0); hybridizing at 50° C., or 65° C., 5×SSC, overnight; followed by washing twice at 65° C. for 20 minutes with each of 2×, 0.5× and 0.2×SSC containing 0.1% SDS.

Low stringency conditions may mean washing in a solution of 2-5×SSC at 50-55° C. Low stringency conditions may also comprise washing in 2×SSC, 0.1% SDS, at 50-55° C., or pre-washing and hybridization for 4 and 12 h, respectively, at 50° C. in 5×SSPE (0.2 M NaH2PO4, pH 7.4, 3M NaCl, 20 mM EDTA), which may contain 2.5×Denhardt's solution, 0.1% SDS, and 0.1 mg/ml denatured salmon sperm DNA.

s. Substantially Identical

"Substantially identical" as used herein may mean that a first and second sequence are at least 50%-99% identical over a region of 8-100 or more nucleotides or amino acids t. Variant "Variant" as used herein in reference to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto; and as used in reference to a polypeptide may mean (i) a portion of a referenced polypeptide sequence; or (ii) a protein that is substantially identical to a referenced protein. A variant may also be a differentially processed protein, such as by proteolysis, phosphorylation, or other posttranslational modification.

u. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223 3, pKK233 3, pDR540, pRIT5 (Pharmacia); Eukaryotic: pWLneo, pSV2cat, pOG44, pXT1, pSG (Stratagene) pSVK3, pBPV, pMSG, pSVL (Pharmacia).

2. HBV NUCLEIC ACID

Provided herein is a HBV-related nucleic acid and variants thereof, which may be derived from the genome of a HBV. The nucleic acid may also be recombinant. The nucleic acid may comprise an open reading frame, which may encode a HBV surface protein or a variant thereof.

a. PreS2 Region

The nucleic acid may comprise a preS2 region. The preS2 region may encode a middle HBV surface protein (MHB), which MHB may comprise the sequence as set forth in Table 1.

TABLE 1

| SEQ ID NO | Middle HBV Surface Protein |
|---|---|
| 1 | 1 mqwnstafhq alqdprvrgl yfpaggsssg tvnpapnias hissisartg dpvtnmenit<br>61 sgflgpllvl qagfflltri ltipqsldsw wtslnflggs pvclgqnsqs ptsnhsptsc<br>121 ppicpgyrwm clrrfiiflf illlclifll vlldyqgmlp vcplipgstt tstgpcktct<br>181 tpaqgnsmfp sccctkptdg nctcipipss wafakylwew asvrfswlsl lvpfvqwfvg<br>241 lsptvwlsai wmmwywgpsl ysivspfipl lpiffclwvy i |

The preS2 region may comprise a sequence as set forth in Table 2. Due to degeneracy in the genetic code, the sequence of the nucleic acid may differ from the sequence as set forth in Table 2, but encode an amino acid sequence identical to the one set forth in Table 1.

TABLE 2

| SEQ ID NO | HBV PreS2 Region |
|---|---|
| 2 | 1 ATGCAGTGGA ATTCCACTGC CTTCCACCAA GCTCTGCAAG ATCCCAGAGT CAGGGGTCTG<br>61 TATTTTCCTG CTGGTGGCTC CAGTTCAGGA ACAGTAAACC CTGCTCCGAA TATTGCCTCT |

TABLE 2-continued

| SEQ ID NO | HBV PreS2 Region |
|---|---|

```
121 CACATCTCGT CAATCTCCGC GAGGACTGGG GACCCTGTGA CGAACATGGA GAACATCACA

181 TCAGGATTCC TAGGACCCCT GCTCGTGTTA CAGGCGGGGT TTTTCTTGTT GACAAGAATC

241 CTCACAATAC CGCAGAGTCT AGACTCGTGG TGGACTTCTC TCAATTTTCT AGGGGGATCA

301 CCCGTGTGTC TTGGCCAAAA TTCGCAGTCC CCAACCTCCA ATCACTCACC AACCTCCTGT

361 CCTCCAATTT GTCCTGGTTA TCGCTGGATG TGTCTGCGGC GTTTTATCAT ATTCCTCTTC

421 ATCCTGCTGC TATGCCTCAT CTTCTTATTG GTTCTTCTGG ATTATCAAGG TATGTTGCCC

481 GTTTGTCCTC TAATTCCAGG ATCAACAACA ACCAGTACGG GACCATGCAA AACCTGCACG

541 ACTCCTGCTC AAGGCAACTC TATGTTTCCC TCATGTTGCT GTACAAAACC TACGGATGGA

601 AATTGCACCT GTATTCCCAT CCCATCGTCC TGGGCTTTCG CAAAATACCT ATGGGAGTGG

661 GCCTCAGTCC GTTTCTCTTG GCTCAGTTTA CTAGTGCCAT TTGTTCAGTG GTTCGTAGGG

721 CTTTCCCCCA CTGTTTGGCT TTCAGCTATA TGGATGATGT GGTATTGGGG GCCAAGTCTG

781 TACAGCATCG TGAGTCCCTT TATACCGCTG TTACCAATTT TCTTTTGTCT CTGGGTATAC

841 ATTTAA
```

(1) PreS2 Initiation Sequence

The preS2 region may comprise a preS2 initiation sequence, from which translation of the MHB may be initiated. The preS2 initiation sequence may comprise the sequence 5'-CTTATGCAG-3' (SEQ ID NO: 3). The preS2 initiation sequence may be altered, which may affect the ratio of MHB to small HBV surface protein (SHB) expressed from the nucleic acid. The preS2 initiation sequence may also comprise a partial Kozak sequence or a Kozak sequence.

(a) Kozak Sequence

The Kozak sequence may be capable of increasing translation from the mutant preS2 initiation sequence. The increased translation may increase the level of MHB produced from the preS2 region. The increased level of MHB may be relative to the level of SHB translated from a S region contained in the nucleic acid. Alternatively, while not being bound by theory, the increased translation of MHB may affect the antigenicity of the resulting protein mixture of SHB and MHB through particle assembly or protein folding that more closely reflects that seen in clinically sourced material.

The Kozak sequence may comprise a consensus sequence, which may be 5'-RNNATGG-3' (SEQ ID NO: 4), wherein N is A, T, G, or C and R is A or G. The Kozak sequence may also comprise the sequence 5'-GCCRCCATGG-3' (SEQ ID NO: 16) or 5'—RCCATGG-3' (SEQ ID NO: 17).

(b) Partial Kozak Sequence

The partial Kozak sequence may be capable of increasing translation from the preS2 initiation sequence. The increased translation may increase the level of MHB produced from the preS2 region. The increased level of MHB may be relative to the level of SHB translated from a S region contained in the nucleic acid. Alternately, the increased translation of MHB may affect the antigenicity of the resulting protein mixture of SHB and MHB through particle assembly or protein folding that more closely reflects that seen in clinically sourced material.

The partial Kozak sequence may comprise the sequence 5'-GNNATGCAG-3' (SEQ ID NO: 18) or 5'-ANNATGCAG-3' (SEQ ID NO: 19). The partial Kozak sequence may also comprise the sequence 5'-GAGATGCAG-3' (SEQ ID NO: 5) or 5'-AAGATGCAG-3' (SEQ ID NO: 6). The sequence of the preS2 region comprising the partial Kozak sequence may comprise a sequence as set forth in Table 3.

TABLE 3

| SEQ ID NO | Middle HBV Surface Protein |
|---|---|

```
7    1 GAGATGCAGT GGAATTCCAC TGCCTTCCAC CAAGCTCTGC AAGATCCCAG AGTCAGGGGT

61 CTGTATTTTC CTGCTGGTGG CTCCAGTTCA GG ACAGTAA ACCCTGCTCC GAATATTGCC

121 TCTCACATCT CGTCAATCTC CGCGAGGACT GGGGACCCTG TGACGAACAT GGAGAACATC

181 ACATCAGGAT TCCTAGGACC CCTGCTCGTG TTACAGGCGG GGTTTTTCTT GTTGACAAGA

241 ATCCTCACAA TACCGCAGAG TCTAGACTCG TGGTGGACTT CTCTCAATTT TCTAGGGGGA

301 TCACCCGTGT GTCTTGGCCA AAATTCGCAG TCCCCAACCT CCAATCACTC ACCAACCTCC

361 TGTCCTCCAA TTTGTCCTGG TTATCGCTGG ATGTGTCTGC GGCGTTTTAT CATATTCCTC
```

TABLE 3-continued

| SEQ ID NO | Middle HBV Surface Protein |
|---|---|
| | 421 TTCATCCTGC TGCTATGCCT CATCTTCTTA TTGGTTCTTC TGGATTATCA AGGTATGTTG |
| | 481 CCCGTTTGTC CTCTAATTCC AGGATCAACA ACAACCAGTA CGGGACCATG CAAAACCTGC |
| | 541 ACGACTCCTG CTCAAGGCAA CTCTATGTTT CCCTCATGTT GCTGTACAAA ACCTACGGAT |
| | 601 GGAAATTGCA CCTGTATTCC CATCCCATCG TCCTGGGCTT TCGCAAAATA CCTATGGGAG |
| | 661 TGGGCCTCAG TCCGTTTCTC TTGGCTCAGT TTACTAGTGC CATTTGTTCA GTGGTTCGTA |
| | 721 GGGCTTTCCC CCACTGTTTG GCTTTCAGCT ATATGGATGA TGTGGTATTG GGGGCCAAGT |
| | 781 CTGTACAGCA TCGTGAGTCC CTTTATACCG CTGTTACCAA TTTTCTTTTG TCTCTGGGTA |
| | 841 TACATTTAA |
| 8 | 1 AAGATGCAGT GGAATTCCAC TGCCTTCCAC CAAGCTCTGC AAGATCCCAG AGTCAGGGGT |
| | 61 CTGTATTTTC CTGCTGGTGG CTCCAGTTCA GGAACAGTAA ACCCTGCTCC GAATATTGCC |
| | 121 TCTCACATCT CGTCAATCTC CGCGAGGACT GGGGACCCTG TGACGAACAT GGAGAACATC |
| | 181 ACATCAGGAT TCCTAGGACC CCTGCTCGTG TTACAGGCGG GTTTTTCTT GTTGACAAGA |
| | 241 ATCCTCACAA TACCGCAGAG TCTAGACTCG TGGTGGACTT CTCTCAATTT TCTAGGGGGA |
| | 301 TCACCCGTGT GTCTTGGCCA AAATTCGCAG TCCCCAACCT CCAATCACTC ACCAACCTCC |
| | 361 TGTCCTCCAA TTTGTCCTGG TTATCGCTGG ATGTGTCTGC GGCGTTTTAT CATATTCCTC |
| | 421 TTCATCCTGC TGCTATGCCT CATCTTCTTA TTGGTTCTTC TGGATTATCA AGGTATGTTG |
| | 481 CCCGTTTGTC CTCTAATTCC AGGATCAACA ACAACCAGTA CGGGACCATG CAAAACCTGC |
| | 541 ACGACTCCTG CTCAAGGCAA CTCTATGTTT CCCTCATGTT GCTGTACAAA ACCTACGGAT |
| | 601 GGAAATTGCA CCTGTATTCC CATCCCATCG TCCTGGGCTT TCGCAAAATA CCTATGGGAG |
| | 661 TGGGCCTCAG TCCGTTTCTC TTGGCTCAGT TTACTAGTGC CATTTGTTCA GTGGTTCGTA |
| | 721 GGGCTTTCCC CCACTGTTTG GCTTTCAGCT ATATGGATGA TGTGGTATTG GGGGCCAAGT |
| | 781 CTGTACAGCA TCGTGAGTCC CTTTATACCG CTGTTACCAA TTTTCTTTTG TCTCTGGGTA |
| | 841 TACATTTAA | b. S Region

The nucleic acid may also comprise a S region, which may encode a small HBV surface protein (SHB), which SHB may comprise the sequence as set forth in Table 4.

TABLE 4

| SEQ ID NO | Small HBV Surface Protein |
|---|---|
| 9 | 1 menitsgflg pllvlqagff lltriltipq sldswwtsln flggspvclg qnsqsptsnh |
| | 61 sptscppicp gyrwmclrrf iiflfilllc lifllvlldy qgmlpvcpli pgstttstgp |
| | 21 cktcttpaqg nsmfpsccct kptdgnctci pipsswafak ylwewasvrf swlsllvpfv |
| | 181 qwfvglsptv wlsaiwmmwy wgpslysivs pfipllpiff clwvyi |

The S region may also comprise the sequence as set forth in Table 5.

TABLE 5

| SEQ ID NO | Small HBV Surface Protein |
|---|---|
| 10 | 1 ATGGAGAACA TCACATCAGG ATTCCTAGGA CCCCTGCTCG TGTTACAGGC GGGGTTTTTC |
| | 61 TTGTTGACAA GAATCCTCAC AATACCGCAG AGTCTAGACT CGTGGTGGAC TTCTCTCAAT |
| | 121 TTTCTAGGGG GATCACCCGT GTGTCTTGGC CAAAATTCGC AGTCCCCAAC CTCCAATCAC |
| | 181 TCACCAACCT CCTGTCCTCC AATTTGTCCT GGTTATCGCT GGATGTGTCT GCGGCGTTTT |
| | 241 ATCATATTCC TCTTCATCCT GCTGCTATGC CTCATCTTCT TATTGGTTCT TCTGGATTAT |
| | 301 CAAGGTATGT TGCCCGTTTG TCCTCTAATT CCAGGATCAA CAACAACCAG TACGGGACCA |
| | 361 TGCAAAACCT GCACGACTCC TGCTCAAGGC AACTCTATGT TTCCCTCATG TTGCTGTACA |
| | 421 AAACCTACGG ATGGAAATTG CACCTGTATT CCCATCCCAT CGTCCTGGGC TTTCGCAAAA |
| | 481 TACCTATGGG AGTGGGCCTC AGTCCGTTTC TCTTGGCTCA GTTTACTAGT GCCATTTGTT |
| | 541 CAGTGGTTCG TAGGGCTTTC CCCCACTGTT TGGCTTTCAG CTATATGGAT GATGTGGTAT |
| | 601 TGGGGGCCAA GTCTGTACAG CATCGTGAGT CCCTTTATAC CGCTGTTACC AATTTTCTTT |
| | 661 TGTCTCTGGG TATACATTTA A |

(1) S Initiation Sequence

The S region may also comprise an S initiation sequence, from which translation of the SHB may be initiated. The S initiation sequence may comprise the sequence 5'-AA-CATGG-3' (SEQ ID NO: 11), and may comprise a Kozak sequence as described herein.

encodes a mutation from methionine to any other amino acid, which may be a leucine. The mutant S initiation sequence may comprise the sequence 5'-AACTTGG-3' (SEQ ID NO: 12) or 5'-AACCTGG-3' (SEQ ID NO: 13).

The preS2 region comprising the mutant S initiation sequence may comprise a sequence as set forth in Table 6.

TABLE 6

| SEQ ID NO | S Region Comprising Mutant Initiation Sequence |
|---|---|
| 14 | AACTTGGAGAACATCACATCAGGATTCCTAGGACCCCTGCTCGTGTTACAGGCGGGGTTTTCTTGTTGACAAGAATCCTCA |
| | CAATACCGCAGAGTCTAGACTCGTGGTGGACTTCTCTCAATTTTCTAGGGGGATCACCCGTGTGTCTTGGCCAAAATTCGCA |
| | GTCCCCAACCTCCAATCACTCACCAACCTCCTGTCCTCCAATTTGTCCTGGTTATCGCTGGATGTGTCTGCGGCGTTTTATCA |
| | TATTCCTCTTCATCCTGCTGCTATGCCTCATCTTCTTATTGGTTCTTCTGGATTATCAAGGTATGTTGCCCGTTTGTCCTCTA |
| | ATTCCAGGATCAACAACAACCAGTACGGGACCATGCAAAACCTGCACGACTCCTGCTCAAGGCAACTCTATGTTTCCCTCATG |
| | TTGCTGTACAAAACCTACGGATGGAAATTGCACCTGTATTCCCATCCCATCGTCCTGGGCTTTCGCAAAATACCTATGGGAGT |
| | GGGCCTCAGTCCGTTTCTCTTGGCTCAGTTTACTAGTGCCATTTGTTCAGTGGTTCGTAGGGCTTTCCCCCACTGTTTGGCTT |
| | TCAGCTATATGGATGATGTGGTATTGGGGGCCAAGTCTGTACAGCATCGTGAGTCCCTTTATACCGCTGTTACCAATTTTCTT |
| | TTGTCTCTGGGTATACATTTAA |

(a) Mutant S Initiation Sequence

The S initiation sequence may comprise a mutant S initiation sequence. The mutant S initiation sequence may also comprise a sequence that may not be a Kozak sequence or partial Kozak sequence. The mutant S initiation sequence may reduce translation of the SHB from the mutant S initiation sequence. The mutant S initiation sequence may not affect MHB translation from the preS2 initiation sequence or mutant preS2 initiation sequence. The mutant S initiation sequence may also not affect antigenicity of the MHB. The mutant S initiation sequence may comprise a nucleic acid that c. PreS1 Region The nucleic acid may also comprise a preS1 region, which may encode a large HBV surface protein (LHB). The LHB may be about 389 amino acids in length, and may be capable of forming part of an HBV envelope.

The preS1 region may also comprise an initiation sequence, from which translation of the LHB may be initiated. The preS1 sequence may comprise a sequence as set forth in Table 7.

TABLE 7

| SEQ ID NO | HBV PreS1 Region | | | | |
|---|---|---|---|---|---|
| 15 | 1 ATGGGAGGTT | GGTCTTCCAA | ACCTCGAAAA | GGCATGGGGA | CAAATCTTTC TGTCCCCAAT |
| | 61 CCCCTGGGAT | TCTTCCCCGA | TCATCAGTTG | GACCCTGCAT | TCAAAGCCAA CTCAGAAAAT |
| | 121 CCAGATTGGG | ACCTCAACCC | ACACAAGGAC | AACTGGCCGG | ACGCTCACAA GGTGGGAGTG |
| | 181 GGAGCATTCG | GGCCAGGGTT | CACCCCTCCC | CATGGGGGAC | TGTTGGGGTG GAGCCCTCAG |
| | 241 GCTCAGGGCA | TACTCACATC | TGTGCCAGCA | GCTCCTCCTC | CTGCCTCCAC CAATCGGCAG |
| | 301 TCAGGAAGGC | AGCCTACTCC | CTTATCTCCA | CCTCTAAGGG | ACACTCATCC TCAGGCCATG |
| | 361 CAGTGGAATT | CCACTGCCTT | CCACCAAGCT | CTGCAAGATC | CCAGAGTCAG GGGTCTGTAT |
| | 421 TTTCCTGCTG | GTGGCTCCAG | TTCAGGAACA | GTAAACCCTG | CTCCGAATAT TGCCTCTCAC |
| | 481 ATCTCGTCAA | TCTCCGCGAG | GACTGGGGAC | CCTGTGACGA | ACATGGAGAA CATCACATCA |
| | 541 GGATTCCTAG | GACCCCTGCT | CGTGTTACAG | GCGGGGTTTT | TCTTGTTGAC AAGAATCCTC |
| | 601 ACAATACCGC | AGAGTCTAGA | CTCGTGGTGG | ACTTCTCTCA | ATTTTCTAGG GGGATCACCC |
| | 661 GTGTGTCTTG | GCCAAAATTC | GCAGTCCCCA | ACCTCCAATC | ACTCACCAAC CTCCTGTCCT |
| | 721 CCAATTTGTC | CTGGTTATCG | CTGGATGTGT | CTGCGGCGTT | TTATCATATT CCTCTTCATC |
| | 781 CTGCTGCTAT | GCCTCATCTT | CTTATTGGTT | CTTCTGGATT | ATCAAGGTAT GTTGCCCGTT |
| | 841 TGTCCTCTAA | TTCCAGGATC | AACAACAACC | AGTACGGGAC | CATGCAAAAC CTGCACGACT |
| | 901 CCTGCTCAAG | GCAACTCTAT | GTTTCCCTCA | TGTTGCTGTA | CAAAACCTAC GGATGGAAAT |
| | 961 TGCACCTGTA | TTCCCATCCC | ATCGTCCTGG | GCTTTCGCAA | AATACCTATG GGAGTGGGCC |
| | 1021 TCAGTCCGTT | TCTCTTGGCT | CAGTTTACTA | GTGCCATTTG | TTCAGTGGTT CGTAGGGCTT |
| | 1081 TCCCCCACTG | TTTGGCTTTC | AGCTATATGG | ATGATGTGGT | ATTGGGGGCC AAGTCTGTAC |
| | 1141 AGCATCGTGA | GTCCCTTTAT | ACCGCTGTTA | CCAATTTTCT | TTTGTCTCTG GGTATACATT |
| | 1201 TAA | | | | |

3. HBV POLYPEPTIDE

Provided herein is a polypeptide, which may be encoded by a HBV-related nucleic acid. The polypeptide may be a HBV protein or a variant thereof. The HBV protein may be a HBV surface protein, and may be recombinant. The polypeptide may comprise a label.

a. Middle Hepatitis B Virus Surface Protein (MHB)

The HBV protein may be a MHB, which may be about 281 amino acids in length. The MHB may contain 226 amino acids of a small HBV surface protein encoded by the S region, and may contain an additional 55 amino acids encoded by the preS2 region. The MHB may be glycosylated. The MHB may be capable of forming part of an HBV envelope, which may expose the MHB on the surface of an HBV particle.

The MHB may comprise a MHB epitope, which may be antigenic or a target of immune surveillance. The MHB may be at a detectable concentration, which may be between $1 \times 10^{-12}$ to $1 \times 10^{-2}$ gms. The MHB may be detectable with an anti-MHB antibody such as a monoclonal antibody, which may be 116-34 (ATCC Deposit No. HB-10122).

b. Small Hepatitis B Surface Protein (SHB)

The HBV protein may be a SHB, which may be about 226 amino acids in length. The SHB may also be glycosylated. The SHB may be capable of forming part of an HBV envelope, which may expose the SHB on the surface of an HBV particle. The SHB may comprise a SHB epitope, which may be antigenic or a target of immune surveillance.

The SHB epitope may be part of an "a" determinant as disclosed in U.S. Pat. Nos. 5,925,512 or 7,141,242, the contents of which are incorporated herein by reference. The "a" determinant may comprise at least five epitopes, which may be partially overlapping or non-overlapping.

The SHB epitope may be a mutant, which may affect the antigenicity of the SHB epitope. The mutant SHB epitope may be more common in certain human populations. For example, the mutant SHB epitope may be more common among liver transplant patients on monoclonal anti-a antibody therapy, or patients in Italy or Japan vaccinated against HBV. The mutant SHB epitope may be a two amino acid insertion at position 122 of the SHB, such as NT or RA, a RGA amino acid insertion at position 123 of the SHB, or a NSTGPCTT (SEQ ID NO: 26) amino acid insertion at position 124 of the SHB, or a T123A, G145R, or P120G mutation, or a combination thereof, as described in U.S. Pat. Nos. 5,925, 512 or 7,141,242, the contents of which are incorporated herein by reference.

The antigenicity of the SHB epitope may be reduced, which may allow an HBV comprising the mutant SHB epitope to escape immune surveillance. The SHB may be at a detectable concentration, which may be between $1 \times 10^{-12}$ gms. The SHB may be detectable by an anti-SHB antibody, which may be H166, H57, H53, H40, H35, or similar antibodies.

4. HBV COMPOSITION

Provided herein is a HBV composition, which may comprise the HBV protein, and may also comprise the HBV-related nucleic acid. The HBV composition may also comprise MHB and SHB at a ratio between 1:1000 and 1000:1. The composition may be used to determine the binding or quality of an antibody to a HBV protein, or the quality of a kit comprising an antibody to the HBV protein, or comprising a HBV protein.

5. VECTOR

Provided herein is a vector, which may comprise a HBV-related nucleic acid. The nucleic acid may be operably linked to a promoter, which may be capable of expressing a polypeptide encoded by the nucleic acid. The vector may also comprise a selectable marker.

The vector may also comprise a fusion sequence, which may be capable of being translated in frame with the HBV-related nucleic acid. The fusion sequence may encode a portion of a fusion protein such as beta-galactosidase (B-gal), superoxide dismutase 9SOD), or CMP-KDO synthetase (CKS), as described in European Pat. Pub. No. 0196056, Published Oct. 1, 1986, European Pat. Pub. No. 0331961, published Sep. 13, 1989, the contents of which are incorporated herein by reference.

1. Host Cell

Provided herein is a host cell, which may comprise the vector. The host cell may be capable of expressing a polypeptide encoded by the vector. The vector may be transiently transfected or stably transfected or integrated into the host cell. Transient transfection may be by virtue of the vector not replicating and rarely integrating in the host cell.

Stable transfection or integration may be by introducing the vector, which may integrate into the host cell genome or may autonomously replicate in the host cell. Stable transfection or integration may be selected for through the use of a selectable marker located on, or transfected with, the vector, followed by selection for a host cell expressing the marker. In stable integration, the site of vector integration may occur randomly within the host cell genome or may be targeted through the use of a vector which comprises a region of homology with the host cell genome sufficient to target recombination with an endogenous locus in the host cell genome. Where constructs are targeted to the endogenous locus, all or some of the transcriptional and translational regulatory regions may be provided by the endogenous locus.

The vector may be introduced into the host cell by transfection, transformation, or electroporation, as described in Sambrook et al. (ed.) (Molecular Cloning: A Laboratory Manual, $2^{nd}$ ed. Vol. 1-3, Cold Spring Harbor Laboratory Press, 1983), the contents of which incorporated herein by reference.

7. MAKING POLYPEPTIDE

Provided herein is a method of making the polypeptide. The polypeptide may be synthesized, or it may be expressed in the host cell. Expression from the host cell may be by culturing the host cell under suitable conditions permitting expression of the polypeptide. Expression may be from the vector, which may contain an expression signal functional in the host cell. Expression may also be accomplished by inducing the activity of a regulatable promoter operably linked to the nucleic acid. Expression may also be from the vector, which may comprise a HBV-related nucleic acid and a fusion sequence.

The expressed polypeptide, which may comprise a HBV polypeptide and a portion of a fusion protein, may be isolated from lysed cells or from a culture medium, and may be purified to the extent needed for the intended use of the expressed polypeptide. Purification may be by techniques known in the art, and may include salt fractionation, chromatography on an ion exchange resin, affinity chromatography, or centrifugation. The expressed polypeptide may be used as a diagnostic reagent. The expressed polypeptide may also be useful for isolating and detecting HBV.

8. KIT

Provided herein is a kit, which may comprise a reagent such as a HBV-related nucleic acid, the vector, the host cell, the HBV composition, a candidate antibody or a combination thereof. For example, the kit may be used to express a HBV polypeptide, which may comprise the vector, an agent capable of inducing expression of the HBV protein encoded by the vector, and a HBV composition comprising the HBV protein at a known concentration for use as a positive control. The kit may also comprise a host cell suitable for transformation with the vector. The kit may also include an antibody capable of detecting the HBV protein for use in confirming expression of the HBV protein from the vector.

The kit may also be used to determine the binding or quality of a candidate antibody to a HBV protein. The kit may comprise the HBV composition and a control anti-HBV antibody capable of binding the HBV protein, which may be used to compare to the binding of the candidate antibody. The kit may also comprise a solid substrate capable of binding to a protein fragment fused to the HBV protein for use in isolating the expressed HBV protein.

The kit may also comprise a detection antibody capable of binding to the anti-HBV antibody and comprising a label, which may be used to measure the binding of the control anti-HBV antibody or candidate antibody to the HBV protein. The kit may also comprise a detection reagent that is capable of inducing the label to generate a signal.

The kit may also comprise additional reagents such as buffers and salts, which may be required for transforming the vector into the host cell, inducing expression of the HBV protein from the vector, promoting or preventing protein-protein interactions, or inducing or blocking the label in generating a signal. The kit may further comprise one or more containers, such as vials or bottles, with each container containing a separate reagent. The kit may also comprise written instructions, which may describe performance of a method or assay described herein.

9. DETERMINING BINDING OF AN ANTIBODY

Provided herein is a method of determining the binding of an antibody, which may comprise determining the level of a candidate antibody binding to a HBV polypeptide. The method may be by a general format comprising: (1) presenting the HBV composition on a solid phase, allowing a test sample containing the candidate antibody to react with the HBV composition, and detecting the candidate antibody bound to the HBV composition with an anti-human antibody coupled to a label; or (2) binding an anti-human antibody to the solid phase, allowing a sample comprising the candidate antibody to react with the bound candidate antibody, and then adding the HBV composition comprising a label in order to detect candidate antibody present in the sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

Determining antibody binding may also comprise: (a) contacting a test sample suspected of containing the candidate antibody with the HBV composition; and (b) detecting the presence of the complex and thus candidate antibody present in the test sample. Measuring candidate antibody may also comprise: (a) contacting the test sample suspected of containing the candidate antibody with the HBV composition for a time and under conditions sufficient to allow the formation of antibody/antigen complexes; (b) adding a conjugate to the resulting antibody/antigen complexes for a time and under conditions sufficient to allow the conjugate to bind to the bound antibody, the conjugate comprising an antibody (directed against the HBV composition) attached to a label; and (c) detecting the presence of the candidate antibody which may be present in the test sample by detecting the signal generated by the label. A control or calibrator may also be used which binds to the HBV composition.

Determining antibody binding may further comprise: (a) contacting the test sample suspected of containing the candidate antibody with anti-antibody specific for the candidate antibody, under time and conditions sufficient to allow the formation of anti-antibody/antibody complexes; (b) adding the HBV composition to the resulting anti-antibody/antibody complexes for a time and under conditions sufficient to allow the HBV composition to bind to the antibody; (c) adding a conjugate to the resulting anti-antibody/antibody/HBV composition complexes, the conjugate comprising a HBV composition comprising a monoclonal or polyclonal antibody attached to a label, the monoclonal or polyclonal antibody being directed against the HBV composition; and (d) detecting the presence of the candidate antibody which may be present in the test sample by detecting the signal generated by the label. A control or calibrator may be used which comprises antibody to the anti-antibody.

Determining antibody may also be by a method as described in U.S. Pat. Nos. 5,925,512 or 7,141,242, the contents of which are incorporated herein by reference.

a. Candidate Antibody

The candidate antibody may be capable of binding to a HBV protein. The HBV protein may be a wild-type HBV protein, or a variant HBV protein which may be a mutant HBV protein.

The candidate antibody may be capable of distinguishing between a wild-type HBV protein and a variant HBV protein, or between two different HBV variant proteins. The candidate antibody may also be capable of binding to any HBV protein. The candidate antibody may be a 116-34, H166, H57, H53, H40, or H35 monoclonal anti-HBV protein antibody or an antibody of similar epitope recognition.

The candidate antibody may also be capable of binding to a HBV protein epitope such as a MHB epitope, a mutant MHB epitope, a SHB epitope, or a mutant SHB epitope. The candidate antibody may be capable of distinguishing between a first HBV protein epitope and a second HBV protein epitope. The candidate antibody may also be capable of binding to a first HBV protein epitope with higher avidity as compared to a second HBV protein epitope.

The first and second HBV protein epitopes may be at different relative positions within the HBV protein. The first and second HBV protein epitopes may also be variants at the same relative position within a first and second HBV protein, respectively. For example, the variants may be a wild-type SHB epitope and a mutant SHB epitope. The variants may also be two different mutant SHB epitopes.

The candidate antibody may be capable of binding a MHB epitope, but incapable of binding to a SHB epitope. The candidate antibody may also be capable of binding to a MHB epitope with higher avidity than to a SHB epitope.

b. Detection System

The label may be detected using a detection system, which may comprise a solid support adapted to be used by a semi-automated or fully-automated immunoanalyzer. The detection system may deliver the sample and reagents (which may comprise an antibody, a label, a buffer, or the like) to a reaction vessel, perform incubations, and optionally wash an unbound labeled polypeptide from a bound labeled polypeptide, without user intervention, once the sample and reagents are inserted into the system. Such a system may be distinguished from a manual or less-automated system by the ability of the system to perform at least 8, 16, 64 or 128 assays in a 48-hour period without user intervention after inserting the sample and the reagents into the system. The system may also be able to calculate the concentration or quantity of a polypeptide in the sample automatically, without the need for human calculation or input once the samples are loaded into the system.

The detection system may also comprise a cartridge format or test strip assay. The detection system may provide unit-dose loadable assay reagents into a disposable instrument, and the unit-dose may contain all the reagents necessary to assay to detect the polypeptide. The disposable instrument may comprise a plastic housing, which may comprise a disposable membrane-like structure of nylon, nitrocellulose, or other suitable material. The sample may be preprocessed or loaded directly onto a loading zone of the disposable instrument. The sample may then optionally flow across the membrane-like structure through a plurality of zones contained on the membrane. The membrane-like structure may further comprise a detergent or lateral flow-aid, and may also contain an absorbent to collect excess fluid and/or encourage lateral flow across the membrane. The detection system may comprise a multi-pack system in which each pack may comprise sufficient reagents to perform 1, 2, 4, 8, 10, or 12 assays.

The detection system may also comprise a microfluidic device designed to analyze the sample in the microliter range (e.g., less than 4 µL, 12 µL, or 50 µL). The microfluidic device may comprise a flow aids, propulsion device (which may comprise an expansion gel, wax, or gas), nanovalving, or the like to assist the transportation of the sample or assay reagents or both through the microfluidic device.

Of course, it goes without saying that any of the exemplary formats herein, and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063, 081 and published US Patent Applications 20030170881, 20040018577, 20050054078, and 20060160164 (incorporated by reference herein for their teachings regarding same).

10. DETERMINING QUALITY OF AN ANTIBODY

It may be desirable to test the quality of an antibody and verify its ability to bind its target, which may be a HBV protein such as MHB or SHB. Provided herein is a method of determining the quality of the antibody. The test antibody may be from a newly-produced lot of a previously-known anti-HBV antibody, an old lot of a previously-known anti-HBV antibody, or a candidate anti-HBV antibody.

The test antibody may be tested for binding of the antibody to a composition comprising MHB or SHB. The MHB or SHB in the composition may be at a known concentration for use as a control for the binding of the test antibody. Binding of the test antibody to the composition may be determined, and the level of binding may be compared to a predetermined value. The predetermined value may be a Kd of $1\times10^{-12}$ to $1\times10^{-6}$ M. The predetermined value may also be the level of binding of a control antibody to the composition.

A level of binding of the test antibody compared to the predetermined value may indicate the quality of the test antibody. A level of binding above the predetermined value may indicate that the test antibody may be useful in detecting a HBV protein, and a level below the predetermined value may indicate that the test antibody is of poor quality and is not as desirable for use in detecting the HBV protein. The method for determining the quality of the antibody may also be useful in determining the quality of a kit comprising an anti-HBV antibody.

The present invention has multiple aspects, illustrated by the following non-limiting examples.

EXAMPLE 1

Constructing a PreS2 Nucleic Acid

The MHB or SHB sequences from an Abbott proprietary plasmid (Coleman, et al. 1999. J Med. Virol. 59:19-24) were transferred into the pcDNA3.1+ plasmid (Invitrogen) using Hind III and Not I restriction sites to generate the MHB and SHB plasmids.

Figure 3:
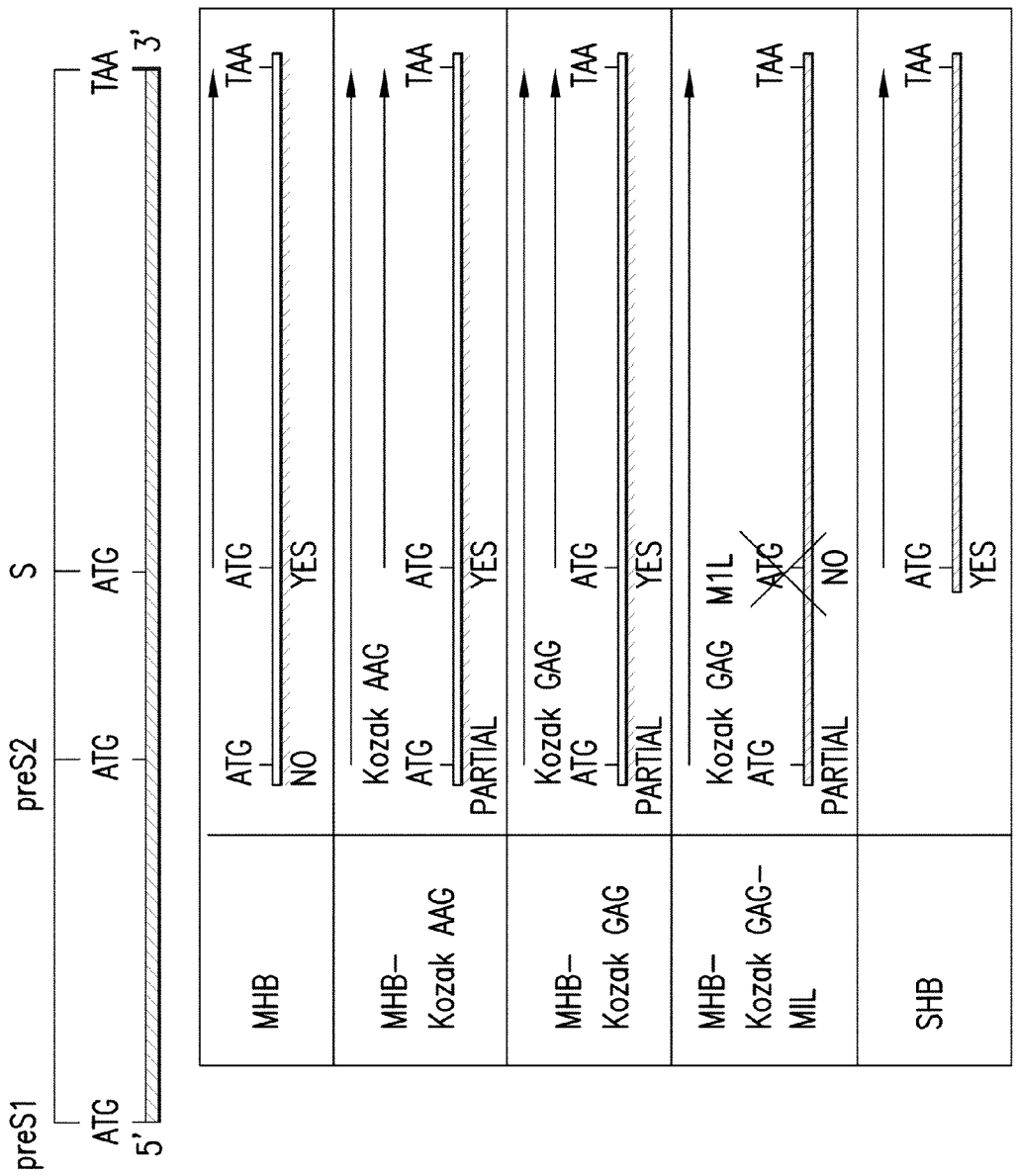
FIG. 3 is a schematic of preS1 open reading frame mutants and their resulting protein expression.

The Kozak GAG, Kozak AAG and M1L mutants (FIG. 3) were generated using the QuikChange II Site-Directed Mutagenesis kit (Stratagene) according to the manufacturer's instructions. The Kozak GAG primers (5'-ggA ATT CCA CTg CAT CTC CTT AAg TTT AAA CgC-3' (SEQ ID NO: 20) and 5'-gCg TTT AAA CTT AAg gAg ATg CAg Tgg AAT TCC-3' (SEQ ID NO: 21)) and Kozak AAG primers (5'-ggA ATT CCA CTg CAT CTT CTT AAg TTT AAA CgC-3' (SEQ ID NO: 22) and 5'-gCg TTT AAA CTT AAg AAg ATg CAg Tgg AAT TCC-3' (SEQ ID NO: 23)) were used to make mutations in the MHB template. The M1L primers (5'-gTg ATg TTC TCC AAg TTC gTC ACA gg-3' (SEQ ID NO: 24) and 5'-CCT gTg Acg AAC TTg gAg AAC ATC AC-3' (SEQ ID NO: 25)) were used to make the M1L mutation in the MHB template containing the Kozak GAG mutation.

All plasmids were sequenced to verify the presence of the mutation and the MHB or SHB sequence.

EXAMPLE 2

Expressing MHB and SHB Using a PreS2 Nucleic Acid

COS-7 cells (ATCC) were cultured at 37° C. in 5% $CO_2$ in Dulbecco's Modified Eagle Medium (DMEM) supplemented with 10% fetal bovine serum (FBS) and 1× antibiotic-antimycotic (AbAm, Invitrogen). For transient transfection, the cells were plated into 2 mL of antibiotic-antimycotic free DMEM/10% FBS at a density of 350,000 cells/35 mm well. The following day, 4 ug of plasmid was diluted into 250 uL of Opti-MEM I Reduced Serum Medium (Invitrogen) and mixed gently. 12 uL of Lipofectamine 2000 (Invitrogen) was diluted into 250 uL of Opti-MEM, mixed gently and incubated for 5 min. The diluted DNA was mixed with the diluted Lipofectamine 2000, incubated for 20 min and added to the cells. After four to six hour incubation at 37° C., the cells were rinsed with 2 mL of DMEM/10% FBS/AbAm and an additional 2 mL of media was added. The cell culture supernatant was harvested three days after transfection.

EXAMPLE 3

Detecting MHB and SHB Using Anti-HBV Antibodies

Wild type and mutant proteins were produced in COS-7 cells transfected with the following plasmids: MHB, MHB-Kozak GAG, MHB-Kozak GAG, MHB-M1L and wild type SHB. Three days post transfection, the cell culture supernatants were harvested and diluted 1:10 in normal human plasma for assay testing.

Auszyme Monoclonal assay and bead assays:

Samples and assay positive/negative controls were run using assay procedure C according to the Auszyme Monoclonal (Abbott Laboratories) package insert. Additional bead assays were run using a panel of antibodies as the capture reagent, including H53, H57, H166 and 116-34 monoclonal antibodies. Goat anti-HBs conjugate was used as the detection reagent. The data represents a total of 2-9 replicates from 1-3 independent transfections.

ARCHITECT HBsAg assay:

Samples and assay positive/negative controls were run according to the Architect HBsAg (Abbott Laboratories) package insert. The data represents a total of 2-9 replicates from 1-3 independent transfections.

Figure 4:
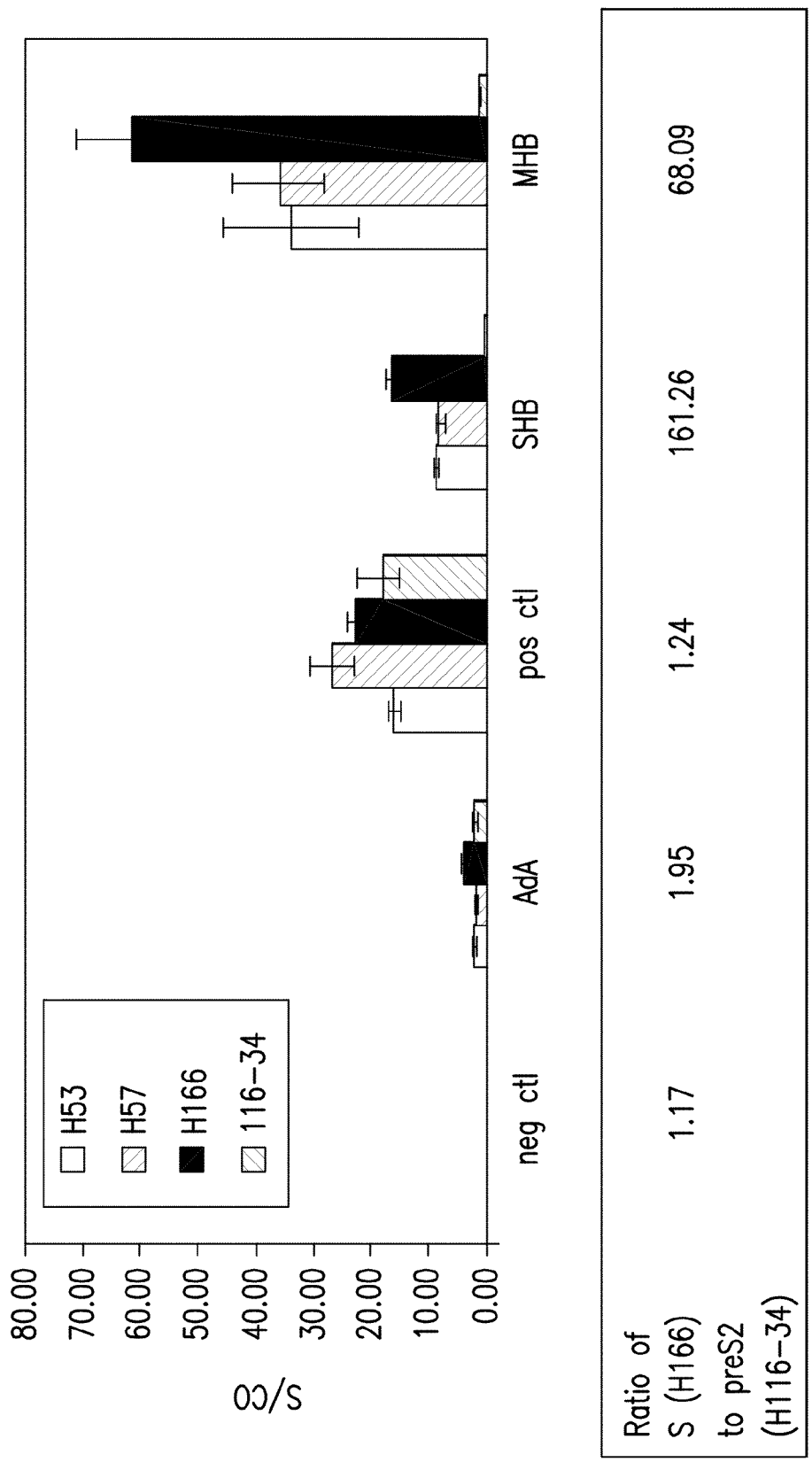
FIG. 4 shows epitope mapping of naturally occurring HBV surface antigens AdA and a positive control using various anti-HBV surface protein antibodies.

As shown in FIG. 4, epitope mapping of naturally occurring HBV surface antigen (HBsAg) samples AdA and the Auszyme Monoclonal kit positive control (pos ctl) showed binding of antibodies to the SHB region (H53, H57 and H166) and to pre-S2 (116-34). The ratio of SHB (H166 antibody signal) to preS2 (116-34 antibody signal) ranged from 1.24-1.95 for these samples. As a control, samples of the Auszyme Monoclonal kit negative control (neg ctl), diluent, untransfected cells and transfection of a plasmid with no HBsAg insert showed no reactivity to the antibodies (data not shown). As expected, the expression of SHB protein showed binding of antibodies directed to the SHB region only (H53, H57 and H166). Recombinant HBsAg produced by transfection with the MHB plasmid showed a significant reduction in preS2 epitope reactivity with a ratio of 68.09.

Figure 5:
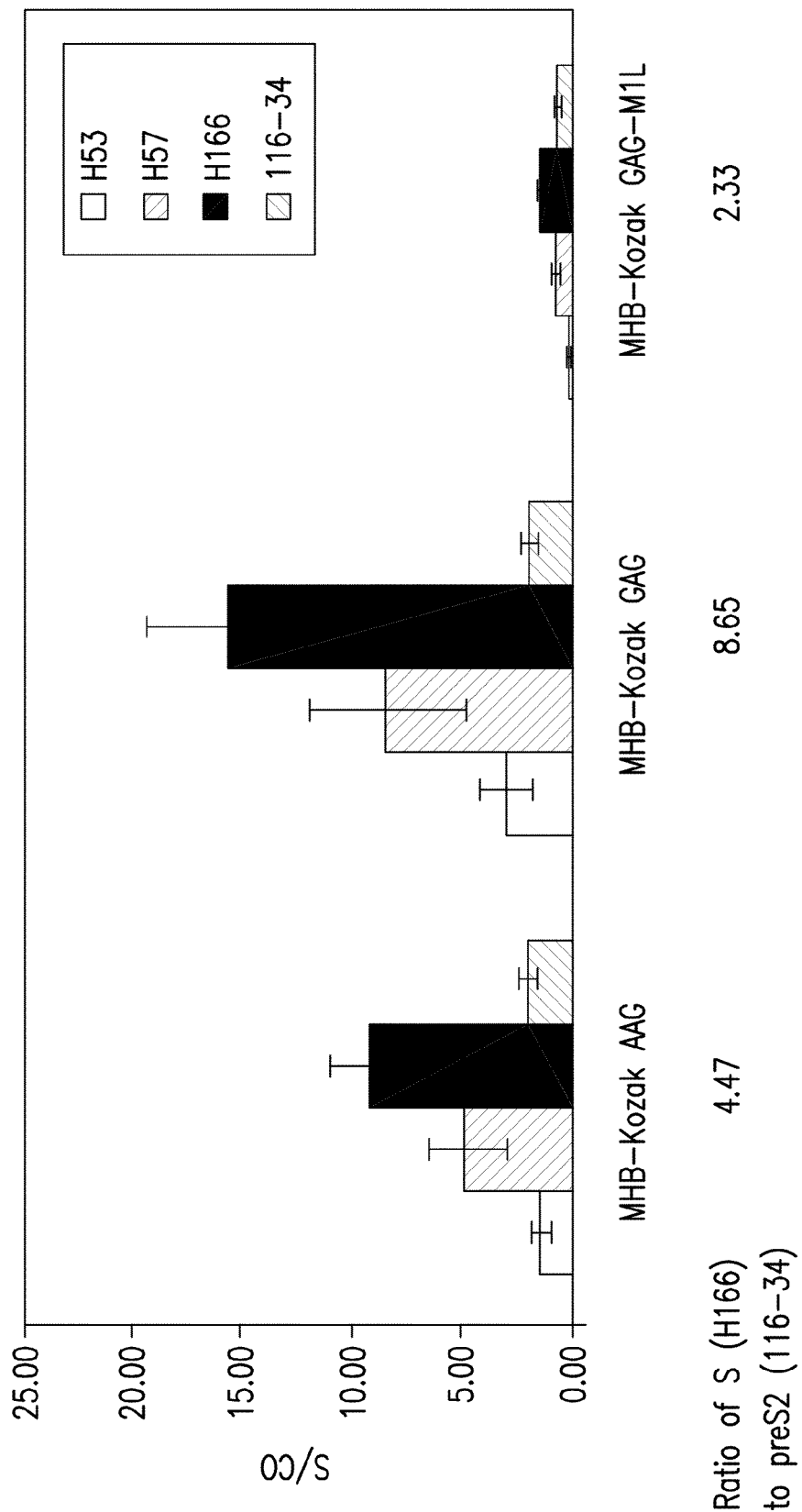
FIG. 5 shows antigenicity of a preS2-encoded protein produced from mutant preS2 sequences as measured using various anti-HBV surface protein antibodies.

In an attempt to increase preS2 reactivity to levels equivalent to naturally occurring HBsAg samples, the Kozak sequence mutants MHB-Kozak GAG and MHB-Kozak AAG were produced to introduce a partial Kozak sequence at the preS2 initiation site. When a transfection was performed using these samples, the protein expressed showed improved signal to the 116-34 preS2 antibody compared to SHB antibody detection (H53, H57, H166) but the overall antigenicity was reduced to approximately 25% of the initial transfection, as shown in FIG. 5. The ratio of SHB to preS2 ranged from 4.47-8.65 for these proteins, which approaches the ratio of naturally occurring samples.

Introducing a knock-out mutation (M1L) at the S initiation site in the MHB-Kozak GAG plasmid to produce only preS2 protein resulted in an even lower reduction in overall antigenicity as shown in FIG. 5. This reduction might be due to intracellular antigen retention or degradation.

The Abbott on-market HBsAg immunoassays (Auszyme Monoclonal and ARCHITECT HBsAg) detected all of the wild type and mutant proteins (FIG. 6). The naturally occurring samples AdA and the appropriate kit positive control (pos ctl) were also detected. Negative controls including pcDNA (plasmid without the MHB sequence), untransfected cells (UTF), the diluent (plasma) and the appropriate kit negative control (neg ctl) were not detected by these assays. These data suggest that the appropriate immunoreagent configuration can detect all mutants, including the M1L mutant.

The invention claimed is:

1. An isolated nucleic acid molecule encoding a middle Hepatitis B virus surface protein (MHB), wherein the nucleotide sequence of said molecule comprises a preS2 initiation sequence, wherein said preS2 initiation sequence starts with AAG or GAG nucleic acid sequence from the 5' end and before the initiation codon ATG of the preS2.

2. The nucleic acid molecule of claim 1, wherein the nucleotide sequence of the nucleic acid molecule comprises SEQ ID NO: 7.

3. The nucleic acid molecule of claim 1, wherein the nucleotide sequence of the nucleic acid molecule comprises SEQ ID NO: 8.

4. The isolated nucleic acid molecule of claim 1, wherein the nucleic acid molecule further comprises a nucleotide sequence encoding a small Hepatitis B virus surface protein (SHB).

5. A vector comprising the nucleic acid molecule of claim 1.

6. An isolated host cell comprising the vector of claim 5.

7. A composition comprising isolated, recombinant MHB at a concentration of $1\times10^{-12}$ to $1\times10^{-2}$ gms.

8. The composition of claim 7, wherein the composition further comprises isolated, recombinant SHB.

9. The composition of claim 8, wherein the SHB is at a concentration of $1\times10^{12}$ to $1\times10^{-2}$ gms.

10. The composition of claim 8, wherein the ratio of MHB to SHB is between 1:1000 and 1000:1.

11. A kit comprising the vector of claim 5.

12. A kit comprising the host cell of claim 6.

13. A kit comprising the composition of claim 7.

* * * * *

UNITED STATES PATENT AND TRADEMARK OFFICE
CERTIFICATE OF CORRECTION

PATENT NO.       : 8,138,318 B2
APPLICATION NO.  : 12/209093
DATED            : March 20, 2012
INVENTOR(S)      : Coleman et al.

Page 1 of 1

It is certified that error appears in the above-identified patent and that said Letters Patent is hereby corrected as shown below:

Column 40, line 55, claim 9: "$1 \times 10^{12}$" to read as --$1 \times 10^{-12}$--

Signed and Sealed this
Sixth Day of November, 2012

David J. Kappos
*Director of the United States Patent and Trademark Office*